(12) United States Patent
Han

(10) Patent No.: US 10,071,111 B1
(45) Date of Patent: Sep. 11, 2018

(54) NANOEMULSION SYNTHETIC RED BLOOD CELLS HAVING SEQUENTIALLY FORMED CALCIUM PHOSPHATE COATING AND PREPARATION METHOD THEREOF

(71) Applicant: Kyu-Bum Han, Seoul (KR)

(72) Inventor: Kyu-Bum Han, Seoul (KR)

(*) Notice: Subject to any disclaimer, the term of this patent is extended or adjusted under 35 U.S.C. 154(b) by 0 days.

(21) Appl. No.: 15/473,570

(22) Filed: Mar. 29, 2017

(30) Foreign Application Priority Data

Mar. 10, 2017 (KR) ........................ 10-2017-0030524

(51) Int. Cl.
*A61K 31/085* (2006.01)
*A61K 31/685* (2006.01)
*A61K 9/107* (2006.01)
*A61K 9/00* (2006.01)
*A61K 9/14* (2006.01)
*B05D 1/26* (2006.01)
*B05D 3/00* (2006.01)

(52) U.S. Cl.
CPC .......... *A61K 31/685* (2013.01); *A61K 9/0026* (2013.01); *A61K 9/107* (2013.01); *A61K 9/143* (2013.01); *A61K 9/145* (2013.01); *B05D 1/265* (2013.01); *B05D 3/007* (2013.01)

(58) Field of Classification Search
CPC .... A61K 31/085; A61K 9/0026; A61K 9/107; A61K 9/143; A61K 9/145; B05D 1/265; B05D 3/007
See application file for complete search history.

(56) References Cited

U.S. PATENT DOCUMENTS

2012/0164231 A1* 6/2012 Ostafin ............... A61K 9/0026
424/490

OTHER PUBLICATIONS

Han et al, Synthesis of Calcim Phosphate Controllable Coating Thickness on Oil-in-Water Nanoemulsion With Performance if Oxygne Release as Oxygen Carrier, Journal or Biomaterials and Nanbiotechnology, vol. 07, No. 2, 2016.*
Benesch, R.E., et al., "Affinity Labeling of the Polyphosphate Binding Site of Hemoglobin", "Biochemistry", 1972, pp. 3576-3582, vol. 11, No. 19.
Petelska, A.D., et al., "Chapter 5: Physicochemical Insights into Equilibria in Bilayer Lipid Membranes", "Advances in Planar Lipid Bilayers and Liposomes, vol. 3", 2006, pp. 159-162, Publisher: Elsevier, Published in: Liu, A.L., ed.
Sachs, J.N., et al., "Changes in Phosphatidylcholine Headgroup Tilt and Water Order Induced by Monovalent Salts: Molecular Dynamics Simulations", "Biophysical Journal", Jun. 2004, pp. 3772-3782, vol. 86.

(Continued)

*Primary Examiner* — Carlos A Azpuru
(74) *Attorney, Agent, or Firm* — Hultquist, PLLC; Steven J. Hultquist

(57) ABSTRACT

The present invention relates to nanoemulsion type synthetic red blood cells having a calcium phosphate coating of controllable thickness, and to a preparation method thereof. According to the present invention, $Ca^{2+}$ and $PO_4^{2-}$ coating layers are uniformly and sequentially formed using a layer-by-layer (LBL) coating method while controlling the thicknesses of the coating layers. Thus, the oxygen capacity and oxygen release rate of the synthetic red blood cells can be controlled, and the synthetic red blood cells can be retrieved and reused.

12 Claims, 9 Drawing Sheets
(7 of 9 Drawing Sheet(s) Filed in Color)

(56) References Cited

OTHER PUBLICATIONS

An, K.-B., et al., "Synthesis of Calcium Phosphate Controllable Coating Thickness on Oil-in-Water Nanoemulsion with Performance of Oxygen Release as Oxygen Carrier", "Journal of Biomaterials and Nanobiotechnology", Mar. 31, 2016, pp. 55-63, vol. 7.

* cited by examiner

NANOEMULSION SYNTHETIC RED BLOOD CELLS HAVING SEQUENTIALLY FORMED CALCIUM PHOSPHATE COATING AND PREPARATION METHOD THEREOF

CROSS-REFERENCE TO RELATED APPLICATION

This application claims priority under 35 U.S.C. § 119 of Korean Patent Application No. 10-2017-0030524 filed Mar. 10, 2017. The disclosure of such Korean priority patent application is hereby incorporated herein by reference in its entirety, for all purposes.

TECHNICAL FIELD

The present invention relates to nanoemulsion type synthetic red blood cells having a calcium phosphate coating formed by sequential coating, and a preparation method thereof. More specifically, the present invention relates to nanoemulsion type synthetic red blood cells having a calcium phosphate coating formed by sequential coating, in which a $Ca^{2+}$ coating layer and a $PO_4^{2-}$ coating layer are uniformly and sequentially formed as separate layers by use of a layer-by-layer (LBL) coating method while controlling the thicknesses of the calcium and phosphate coating layers so that the oxygen capacity and oxygen release rate of the synthetic red blood cells can be controlled and the synthetic red blood cells can be retrieved and reused, and to a preparation method thereof.

BACKGROUND ART

Artificial oxygen carriers (AOCs) are synthetic solutions having the ability to bind, transport and unload oxygen in the body. These synthetic solutions lack blood components such as immune cells and coagulation factors, and thus are called red blood cell (RBC) substitutes rather than blood substitutes.

Two types of artificial oxygen carriers are currently being developed: hemoglobin-based oxygen carriers (HBOCs), and synthetic red blood cells (sRBCs).

In order to avoid the spontaneous breakdown and toxicity of hemoglobin directly taken from red blood cells, purified human, animal or recombinant hemoglobin is used as raw materials in preparation of hemoglobin-based oxygen carriers. In addition, pure hemoglobin isolated from red blood cells has a disadvantage in that oxygen is not exactly delivered. To overcome this disadvantage, cross-linking, polymerization, encapsulation and the like should be performed during the preparation process, thus making the preparation process complex and increasing the production cost.

Hemoglobin-based oxygen carriers were approved by the US FDA for use in vertebrate animals, are in clinical phase III for use in humans, and were approved as pharmaceuticals by several countries in South Africa. HBOCs are known to have excellent in vivo stability.

Synthetic red blood cells are synthetic factors that mimic the function of red blood cells. Synthetic red blood cells transport oxygen, effectively deliver therapeutic drugs, and also enhance resolution in image diagnosis due to their ability to transport well-dispersed contrast agents while controlling the release rate. The particle size or oxygen capacity of these synthetic red blood cells is controlled by the amount of materials used in synthesis, or the configuration or structure of the components.

Among synthetic red blood cells, perfluorocarbon (PFC)-based synthetic red blood cells can be heat-treated, are effective for oxygen delivery and carbon dioxide removal, and have an excellent ability to diffuse in blood because they have a size equal to 1/40 of red blood cells. However, these PFC-based synthetic red blood cells have a shortcoming in that they have poor stability because they are cleared in vivo within 48 hours.

In an attempt to improve the stability, U.S. Patent Publication No. 2012-164231 discloses synthetic red blood cells prepared by emulsifying perfluorooctyl bromide or perfluorodecalin with 1,2-dioleoyl-sn-glycero-3-phosphate (DOPA) or an equivalent lipid with a density higher than that of red blood cells, passing the emulsion multiple times through an extrusion membrane to produce submicron structures, coating $Ca^{2+}$ and $PO_4^{2-}$ on the submicron structures to have a thickness of 5-20 nm, and mixing the coated submicron structures with carboxyethylphosphonic acid (CEPA). Herein, the CEPA that is added in the finishing step carboxylates the coating layer and inhibits self-aggregation of the synthetic red blood cells. The perfluorocarbon-based synthetic red blood cells have disadvantages in that, because $Ca^{2+}$ and $PO_4^{2-}$ are added at the same time in the process of coating with $Ca^{2+}$ and $PO_4^{2-}$, most of the added $Ca^{2+}$ and $PO_4^{2-}$ form the ceramic crystal calcium phosphate without being attached to the submicron structures, and thus the yield of coating on the submicron structures is low, and the production process cannot always provide submicron structures having the same coating, and thus has low reproducibility.

Accordingly, the present inventors have made extensive efforts to overcome the problems of conventional synthetic red blood cells, and as a result, have found that, when $Ca^{2+}$ and $PO_4^{2-}$ coating layers are uniformly and sequentially formed while controlling the thicknesses of the $Ca^{2+}$ and $PO_4^{2-}$ coating layers on synthetic red blood cells based on perfluorooctyl bromide, the oxygen capacity and oxygen release rate of the synthetic red blood cells can be controlled and the synthetic red blood cells can be retrieved and reused, thereby completing the present invention.

DISCLOSURE OF INVENTION

It is an object of the present invention to provide nanoemulsion type synthetic red blood cells having a calcium phosphate coating of controllable thickness, in which the oxygen capacity and oxygen release rate of the synthetic red blood cells can be controlled by controlling the thickness of $Ca^{2+}$ and $PO_4^{2-}$ coating layers thereon and the synthetic red blood cells can be retrieved and reused, and a preparation method thereof.

To achieve the above object, the present invention provides synthetic red blood cells, comprising: (A) a lecithin emulsion comprising a perfluorinated compound; and (B) a calcium phosphate (CaP) coating layer consists of a $Ca^{2+}$ coating layer formed on a surface of the lecithin emulsion and a $PO_4^{2-}$ coating layer formed on the $Ca^{2+}$ coating layer, wherein the CaP coating layer consists of 1 to 10 layers.

The present invention also provides a method of preparing synthetic red blood cells by a layer-by-layer coating method, the method comprising: (a) forming a $Ca^{2+}$ coating layer on a surface of an emulsion having a predetermined pore size by adding a solution of a $Ca^{2+}$ ion-containing compound to the emulsion, and then forming a $PO_4^{2-}$ coating layer on the $Ca^{2+}$ coating layer by adding a solution of a $PO_4$2- ion-containing compound; and (b) removing residual ions which are not absorbed into the emulsion by dialysis, wherein the step (b) is performed 1-10 times.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
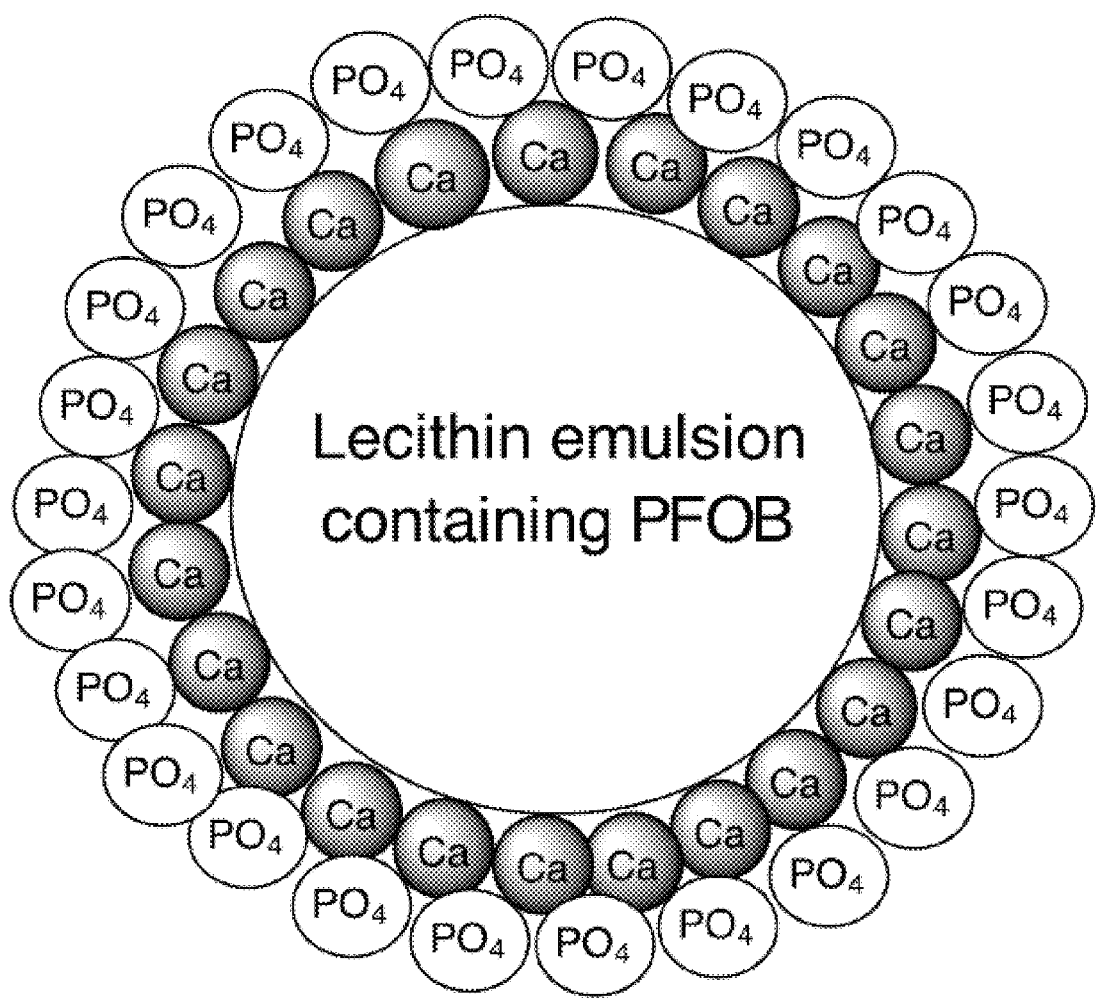
FIG. 1 is a schematic view showing the structure of a synthetic red blood cell prepared by coating $Ca^{2+}$ and $PO_4^{2-}$ on a perfluorooctyl bromide-containing lecithin emulsion.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, it was found that when $Ca^{2+}$ and $PO_4^{2-}$ coating layers are uniformly and sequentially formed while controlling the thicknesses of the $Ca^{2+}$ and $PO_4^{2-}$ coating layers on synthetic red blood cells based on perfluorooctyl bromide, the oxygen capacity and oxygen release rate of the synthetic red blood cells can be controlled and the synthetic red blood cells can be retrieved and reused.

Therefore, in one aspect, the present invention is directed to synthetic red blood cells, comprising: (A) a lecithin emulsion comprising a perfluorinated compound; and (B) a calcium phosphate (CaP) coating layer consists of a $Ca^{2+}$ coating layer formed on a surface of the lecithin emulsion and a $PO_4^{2-}$ coating layer formed on the $Ca^{2+}$ coating layer, wherein the CaP coating layer consists of 1 to 10 layers.

In the present invention, the particle size of the synthetic red blood cells may be 90-800 nm, preferably 150-500 nm, and more preferably 200-300 nm. If the particle size of the synthetic red blood cells exceeds 800 nm, various side effects will be caused. An example of the most common side effect is thrombus, and a side effect such as hypertension, abdominal pain, skin rash or diarrhea occurs. The particle side of the synthetic red blood cells, which can minimize such a side effect, may 200-300 nm.

In the present invention, the thickness of the CaP coating may be 5-100 nm, preferably 5-70 nm, and most preferably 8-40 nm. If the thickness of the CaP coating is within the above range, side effects in the body or the blood vessel will be minimized and the adjustment of the coating thickness can effectively release oxygen or molecules loaded into the particles at a desired time.

In the present invention, the perfluorinated compound may be perfluorooctyl bromide (PFOB), perfluorodecyl bromide (PFDB), perfluorodichlorooctane (PFDCO), perfluorohexane (PFH) or perfluorooctane (PFO), and preferably perfluoroalkyl bromide is used, but is not limited thereto.

Lecithin, a surfactant, which is a phospholipid comprising glycerin phosphate, is composed of a phosphate head and a hydrocarbon chain tail. Lecithin is divided according to a source from which it is extracted. Lecithin may be L-α-phosphatidylcholine extracted from soybean, sunflower, egg yolk or the like, but is not limited thereto.

In another aspect, the present invention is directed to a method of preparing synthetic red blood cells by a layer-by-layer coating method, the method comprising: (a) forming a $Ca^{2+}$ coating layer on a surface of an emulsion having a predetermined pore size by adding a solution of a $Ca^{2+}$ ion-containing compound to the emulsion, and then forming a $PO_4^{2-}$ coating layer on the $Ca^{2+}$ coating layer by adding a solution of a $PO_4^{2-}$ ion-containing compound; and (b) removing residual ions which are not absorbed into the emulsion by dialysis, wherein the step (b) is performed 1-10 times.

The preparation method of the synthetic red blood cells by the layer-by-layer coating method according to an embodiment of the present invention comprises the following steps of:

(a) adding and stirring lecithin, a perfluorinated compound and water to form an emulsion;

(a) extruding the emulsion through a membrane having a pore size of 200-300 nm;

(c) adding a solution of a $Ca^{2+}$ ion-containing compound to the emulsion that having extruded the membrane to form a $Ca^{2+}$ coating layer on the surface of the emulsion, and then adding a solution of a $PO_4^{2-}$ ion-containing compound to form a $PO_4^{2-}$ coating layer on the $Ca^{2+}$ coating layer; and (d) performing dialysis to wash away free ions not adsorbed to the emulsion, wherein step (b) is performed 1-10 times.

Herein, the thickness of the nanoemulsion according to the present invention can be controlled by adjusting the bumber of the coating layers. The thickness of the nanoemulsion can be used for the purpose of controlling the time when oxygen is released in transporting oxygen. The particle size of the synthetic red blood cells may be 90-800 nm, and preferably 200-300 nm. If the particle size thereof is within the above range, the side effects as described above will be minimized, and simultaneously oxygen capacity can be utilized to the maximum.

Figure 2:
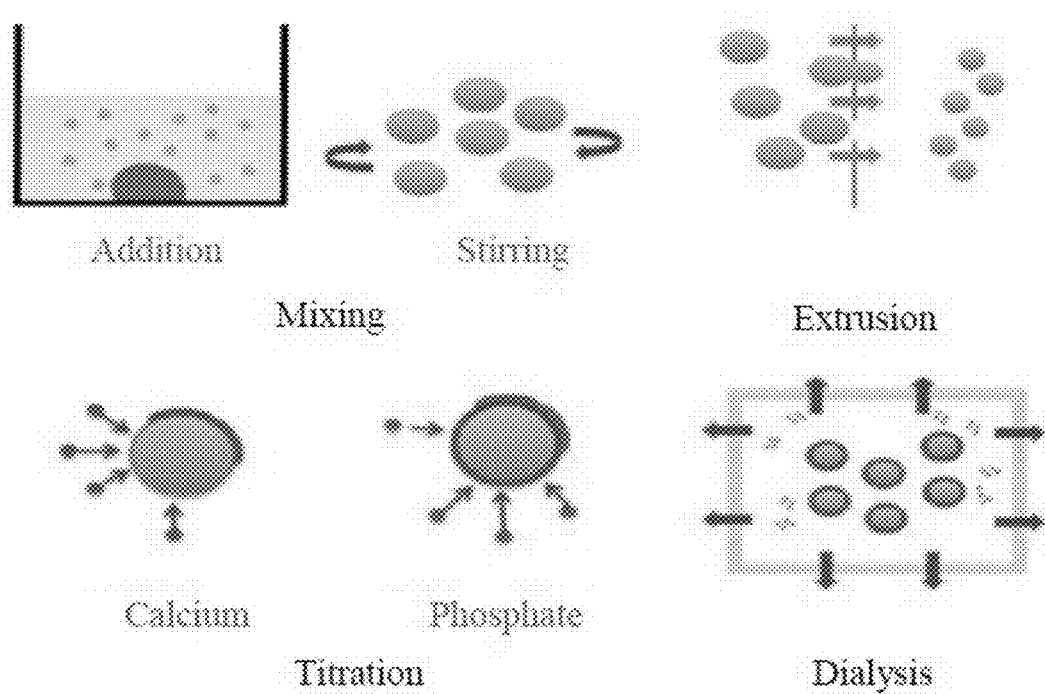
FIG. 2 is a schematic view showing a method of preparing synthetic red blood cells by coating $Ca^{2+}$ and $PO_4^{2-}$ on a perfluorooctyl bromide-containing lecithin emulsion by a layer-by-layer coating method.

In addition, the layer-by-layer coating method according to the present invention will be described in detail with reference FIG. 2.

The layer-by-layer coating method according to an embodiment of the present invention is composed of four steps: mixing, extrusion, titration, and dialysis. Specifically, it may comprise: (a) a step of adding, mixing and stirring lecithin, PFOB and water to form an emulsion; (b) an extrusion step of controlling the size of the emulsion; (c) a titration step of coating $Ca^{2+}$ and $PO_4^{2-}$; and (d) a dialysis step of washing away free unassociated ions.

(a) Addition and Mixing Step

First, lecithin, PFOB and water are added to a beaker, and the mixture is stirred at room temperature. At this time, lecithin (orange), perfluorooctyl bromide (blue) and water (green) are sequentially added to a beaker, and stirred at room temperature to form an emulsion.

(b) Extrusion Step

The mixture is sized to a uniform particle size of about 280 nm. To obtain an emulsion having a uniform size, the produced emulsion is extruded through a membrane having a pore size of 280 nm or less to make the size of the emulsion uniform.

(c) Titration of Ions

In the first step to coat the emulsion surface, calcium chloride (green) is first added to the emulsion suspension. Due to the ionic attractive force, $Ca^{2+}$ ions are adsorbed to the emulsion surface. Next, phosphate (pink color) is added to the suspension, and $PO_4^{2-}$ ions (red) are titrated on the first coating to form a second coating. The $PO_4^{2-}$ ions are associated with the $Ca^{2+}$ ions and adsorbed to the emulsion surface.

(d) Dialysis Step

Remaining ions not adsorbed to the emulsion, including free ions and unassociated ions, are washed away by dialysis.

In the present invention, step (a) may be performed at room temperature. Preferably, it may be performed at a temperature of 20 to 25° C. Step (b) may be performed 7 to 10 times so that the emulsion having a particle size of 280 nm or less can be uniformly dispersed.

In the preparation method of the synthetic red blood cells according to an embodiment of the present invention, the $Ca^{2+}$ ion-containing compound may be one or more selected from the group consisting of calcium chloride, calcium hydroxide, calcium nitride, calcium carbonate, and calcium acetate. The $PO_4^{2-}$ ion-containing compound may be one or more selected from the group consisting of phosphoric acid, potassium phosphate, sodium hydrogen phosphate, and ammonium phosphate.

The concentrations of $Ca^{2+}$ and $PO_4^{2-}$ ion-containing compound that are added during coating may be 5-30 mM, preferably 10-25 mM. If the concentrations of $Ca^{2+}$ and $PO_4^{2-}$ added are higher than 30 mM, the emulsion particles will aggregate so that uniform coating will not occur.

The pH of $Ca^{2+}$ ion-containing compound that is added during coating may be 7.5-12, preferably 8-10, most preferably pH 9. When the pH of $Ca^{2+}$ added is in the above range, a coating with uniform thickness can be formed.

Furthermore, the pH of $PO_4^{2-}$ ion-containing compound may be 7.2-12.6, preferably 8-10, most preferably pH 9. When the pH of $PO_4^{2-}$ ion-containing compound added is in the above range, a coating with uniform thickness can be formed.

If the pHs of $Ca^{2+}$ and $PO_4^{2-}$ added are less than 7.5 and 7.2, respectively, or more than 12 and 12.6, respectively, problems will arise in that a coating with uniform thickness cannot be formed and in that the surface boundary of the emulsion is broken or calcium or phosphate is not adsorbed to the emulsion surface.

In addition, after completion of coating formation, the final pHs of $Ca^{2+}$ and $PO_4^{2-}$ are adjusted to 7.2.

According to the present invention, the emulsion particle can be sized to a desired size, the sized particle can be coated with calcium phosphate, and the stability and the oxygen release/content can be determined. The emulsion mixture is unable to naturally form uniform, dispersed particles, so it is extruded through a polymer membrane under constant pressure. The emulsion is pushed through the membrane seven times in order to ensure that the particles are uniform and dispersed. The result is a reduction in size from 1 μm to 280 nm in diameter. The uniform size and dispersion of the particles are essential for the coating procedures that follow. In order to ensure the optimal dispersion of particles, the zeta-potential is monitored as a function of pH, since some type of surface charge is necessary to avoid flocculation, coalescence, or creaming. The optimal dispersion was found to be at pH 8.8, where a strong negative charge encapsulated the particles. The change in zeta-potential was 32 times greater with calcium than with phosphate, indicating that the soy lecithin molecule had a higher affinity for positively charged calcium over the negative phosphate. The binding coefficient of the calcium ion to soy lecithin was studied, using a Hill Plot, to estimate the amount of the calcium that would be needed for a full coating. The results showed binding of one calcium ion to one soy lecithin molecule. In order to verify the layer-by-layer growth, zeta-potential is used to monitor changes in surface charge. When the calcium ion is added to the emulsion system, the potential increases, and it returns to its initial value when the phosphate ion is added. Using these monitoring techniques, the emulsion particles are coated with calcium phosphate to various thicknesses ranging from 8 nm to 38 nm. Using a fast mixing method, with a stopped-flow apparatus and hemoglobin, oxygen release/content of the coated emulsion is measured. Combining these tools, the oxygen from the particle is measured quickly and accurately. When the thickness of the coating on the emulsion particle is increased, the amount of oxygen released over a given time decreases from 77 μM to 45 μM.

Figure 7:
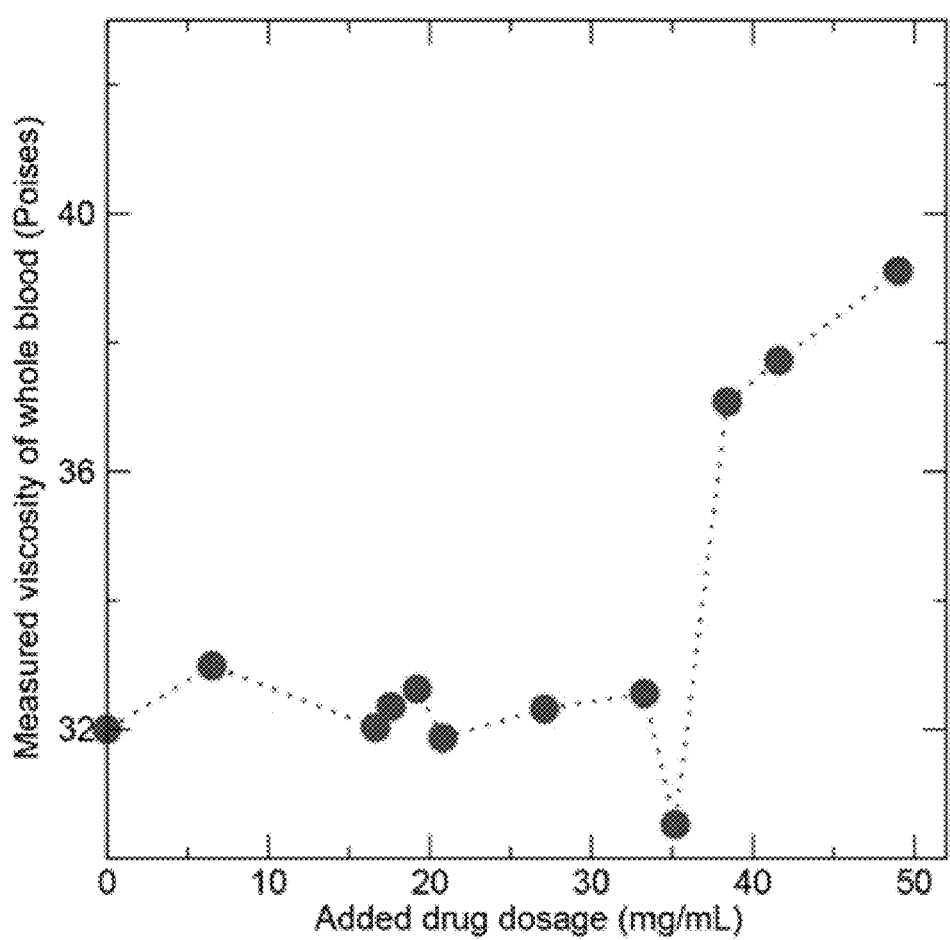
FIG. 7 is a graph showing the maximum dosage of calcium phosphate (CaP)-coated emulsion particles according to the present invention.

When nanoemulsion coated with calcium phosphate is mixed with whole blood, if the nanoemulsion reacts with the protein or the like in the whole blood, coagulation will occur to increase the viscosity, and if the nanoemulsion destroys the red blood cells in the whole blood (ghost cell), the viscosity will decrease. In addition, if the viscosity does not change even when the nanoemulsion is added, it indicates that the nanoemulsion did not react with the whole blood. FIG. 7 shows the results of measuring the viscosity of whole blood mixed with the nanoemulsion. The maximum dosage was determined from the start point at which the viscosity value changes, and as a result, the maximum dosage of the coated product was 33 mg/mL.

The density of the nanoemulsion is about 2 g/mL, and the density of red blood cells is about 1.1-1.2 g/mL. Due to this difference in density, the nanoemulsion can be separated from whole blood by dialysis after injection into the body. Thus, the nanoemulsion is not retained in the body during life, and can be separated from whole blood at any time point and reused.

In addition, the synthetic red blood cells are prepared as a formulation such as sticking plaster or ointment so that they can be applied to emergency patients.

EXAMPLES

Hereinafter, the present invention will be described in further detail with reference to examples. It will be obvious to a person having ordinary skill in the art that these examples are for illustrative purposes only and are not to be construed to limit the scope of the present invention.

Preparation Example 1: Synthesis of Calcium Phosphate-Coated Nanoemulsion

Soy lecithin and perfluorooctyl bromide (PFOB) were respectively purchased from Avanti Polar Lipids, Inc. (Alabaster, Ala.), and Oakwood Chemical, Inc. (Alabaster, Ala.). Packed red blood cells (RBCs) were obtained from the University Hospital Blood Bank at the University of Utah. The RBCs were washed three times with normal saline before being hemolyzed with a hypotonic phosphate buffer. After centrifugation, a supernatant of hemoglobin solution was obtained.

To synthesize an oil-in-water nanoemulsion, soy lecithin (1.1 mg/g) was added to PFOB (2 vol %) and deionized water. The sample was stirred at 1200 rpm for 30 minutes at room temperature and extruded through a 200-nm pore size membrane, seven times, at 150 psi. A titration method was utilized to optimize the surface charge of the emulsion with hydrochloric acid (HCl, 0.1 M) and to observe the ionic affinity between calcium and phosphate ions; calcium chloride ($CaCl_2$, 3.0 mM, pH 9) and phosphate solution (3.0 mM, pH 9), from phosphoric acid ($H_3PO_4$), were separately titrated into the emulsion suspension. For calcium phosphate coating, the preparation of scheme is shown in FIG. 2. Calcium phosphate (CaP) layers with various coating thicknesses were produced by this layer-by-layer method. First, the emulsion solution was adjusted to pH 9. Then, the calcium chloride (1.4 mM, pH 9) was titrated to the emulsion with the same volume of the emulsion solution. The phosphate solution (1.4 mM, pH 9) was titrated to the mixture for the next layer of coating with the same volume of the emulsion solution. In each titration, the mixture was adjusted to pH 9. This process was repeated for the desired thicknesses. Once the coating process was completed, the mixture was dialyzed for 3 days against deionized water, with a 3,500 MWCO membrane. After dialysis, the suspension was concentrated back to the original concentration using tangential flow filtration (TFF) (KrosFlo® Research lli Tangential Flow Filtration System, Spectrum Laboratories, Inc., Rancho Dominguez, Calif.).

Example 1: Examination of the Characteristics and Stability of Nanoemulsion

The particle size and zeta-potential were characterized by Zetasizer Nano ZS (Malvern, UK). Transmission electron microscope (FEI Tecnai™ TEM) was utilized for morphology observations, where the emulsion was prepared with a negative stain, uranyl acetate (47 mM, 10 μL). The coated and uncoated emulsions (with and without CaP) were observed at 80 keV.

The pH titration test clearly supported the notion that the phosphate group in soy lecithin was the main site of ion interaction. Since the amine group in soy lecithin is a quaternary amine group having three methyl groups and one R group, it is not pH active. The phosphate in the head group of soy lecithin was the only group that was expected to react with a proton. The zeta-potential is a good indicator of the dispersion stability. Near zero mV results in minimal electrostatic repulsion between particles, so the greater absolute value of zeta-potential, the better the stability due to the charge repulsion. From the change in zeta-potential with pH, the isoelectric point (pI) was determined (FIG. 3(a) and FIG. 3(b)). Soy lecithin molecules are zwitterionic due to the positive quaternary amine and the negative phosphate groups (pH dependent), making them ampholytic which means the molecule can obtain equilibrium in either basic or acidic conditions.

Figure 3:
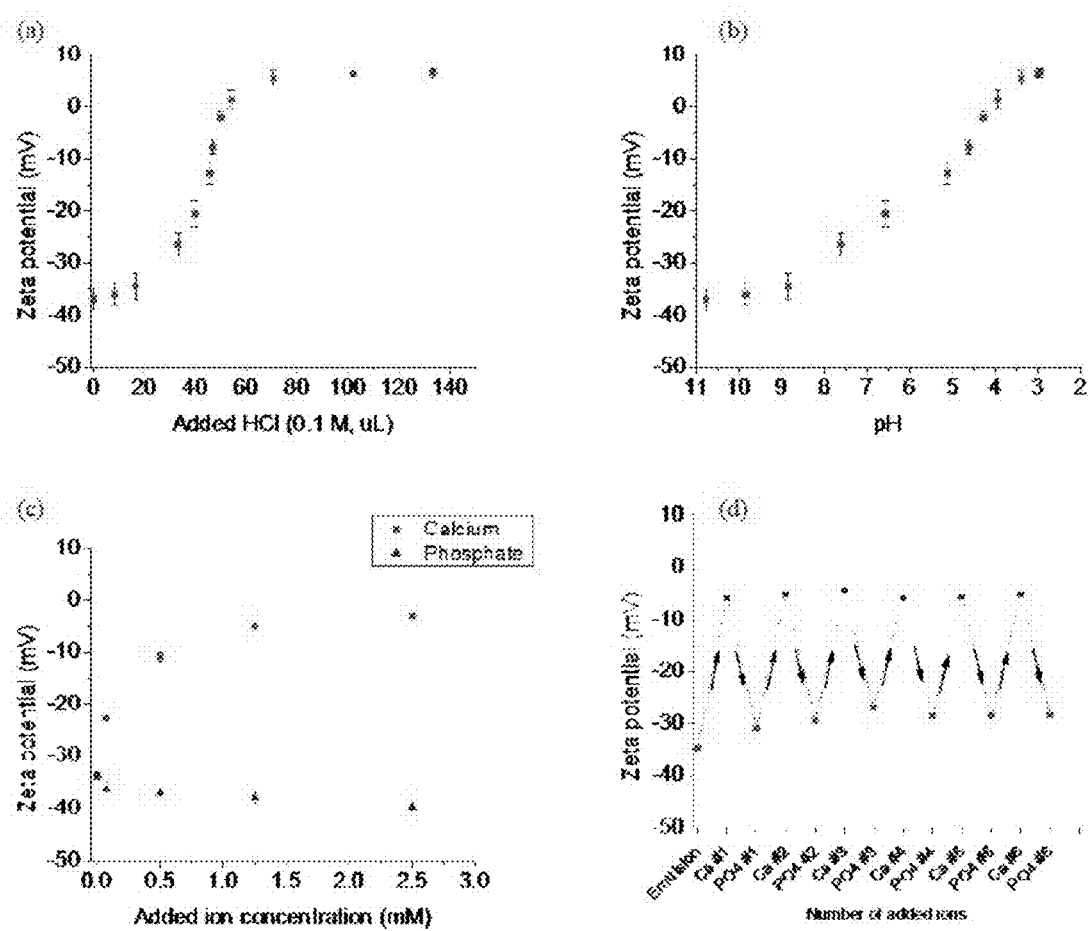
FIG. 3 shows the results of analyzing a calcium phosphate (CaP)-coated emulsion according to the present invention and an uncoated emulsion by transmission electron microscopy (TEM).

FIG. 3(a) shows zeta-potential as a function of added HCl; FIG. 3(b) shows compiled zeta-potential as a function of pH; and FIG. 3(c) shows the ionic affinity of calcium and phosphate to the emulsion surface at pH 9. The zeta-potential curve of the optimized emulsion at pH 9 with calcium and phosphate ions showed the affinity to the emulsion surface by titration with mean and standard deviation in three measurements. The zeta-potential changed from −40 mV to −21 mV by adding calcium, while phosphate changed from −40 mV to −46 mV. The absolute values of the slope in the first three data points were 18 in calcium and 6 in phosphate. FIG. 3(d) shows changes in zeta-potential with the addition of each layer of the calcium phosphate coating. The initial zeta-potential was −35 mV, and the first addition of calcium ion increased the potential to −5 mV. Then, the first addition of phosphate decreased the potential to −30 mV.

A typical emulsion yields a zeta-potential of −38.5 mV at pH 10.6, and upon the addition of acid, the zeta-potential continues to increase until it reached 0 mV (Liu, A. (2006) Acid-Base Equilibria between the Lipid Membrane and Electrolyte Solution. Elsevier, San Diego), at pH 4.1, an isoelectric point in good agreement with a previously reported value. At pH values greater than 8.85, the positively charged quaternary amine of soy lecithin is saturated with free $OH^-$ ions, making the zeta-potential negative. The addition of more protons drives the equilibrium reaction (Le Chatelier Principle) toward the production of more water, and as a result there is an increase in zeta-potential. Once the pH reaches the isoelectric point, the overall electric charge of the head group of soy lecithin is neutral. The zeta-potential starts to plateau at pH 3, which suggests that all of the phosphate groups had been neutralized with protons, resulting in a net positive charge.

The complexity of the array formed by the soy lecithin molecules made it difficult to tell which of the groups, phosphate or quaternary amine, was actually the primary binding ion site. Complicating matters more is the fact that the head group of the molecule is bent, resting at about 90° (Pullman, A. et al., (1994) Biomolecular Structures and Mechanism. Kluwer Academic Publishers, Dordrecht). However, by measuring the zeta-potential through a pH titration, it was concluded that the affinity for free calcium ions toward the soy lecithin phosphate was greater than that of free phosphate ions to the quaternary amine.

The zeta-potential demonstrated an isoelectric point at pH 5.33.

At pH 9 the emulsion system has its lowest zeta-potential at −34 mV. After the addition of calcium cation, the zeta-potential increased to −3 mV, and when phosphate ion ($HPO_4^{2-}$) was added and the zeta-potential only decreased to −39 mV, a change of only 5 mV (FIG. 3(c)). At pH 9, the phosphate group is the dominant functional group for soy lecithin because the quaternary amine has been neutralized by the $OH^-$ anion. When calcium ions were added to the system, the ion associates itself with the phosphate group. The solubility product constant ($K_{sp}$) values at 25° C. of calcium hydroxide ($Ca(OH)_2$) and calcium hydrogen phosphate ($CaHPO_4$) are $5.5 \times 10^{-6}$ and $1 \times 10^{-7}$, respectively (Benesch, R. et al., Biochemistry, 11, 3576-3582). The lower the solubility, the easier it is precipitates. $CaHPO_4$ has a lower Ksp value than $Ca(OH)_2$. Thus, it is easier for the calcium to bind to the phosphate group than the free hydroxide in solution or those adsorbed to the quaternary amine. Even though soy lecithin has a net neutral charge on its head group, it is still able to bind calcium cations. Building a calcium phosphate shell begins with the addition of calcium ions, followed by a dose of phosphate anions, alternating additions of these two species allowed layer-by-layer buildup of the coating. The deposition of each layer was confirmed with zeta-potential (FIG. 2(d)), which showed alternative positive and negative surface charges. The initial zeta-potential of the emulsion was −34 mV, but after the addition of calcium it increased to −5 mV. With the sequential dose of phosphate, the zeta-potential decreased to −30 mV. This same trend continued for each additional layer of calcium and phosphate, confirming the sequential growth process.

Figure 4:
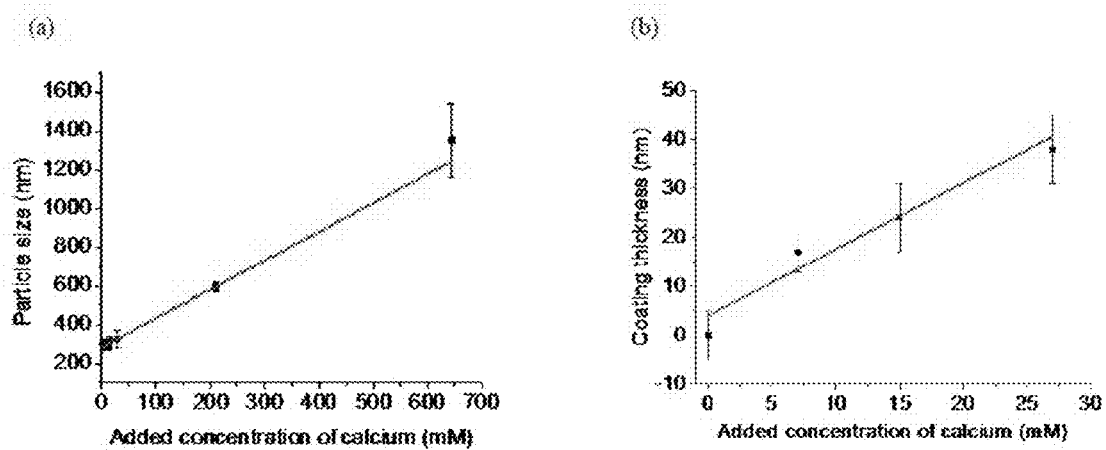
FIG. 4 depicts graphs showing the size of synthetic red blood cells as a function of the concentration of calcium added in calcium phosphate coating according to the present invention.

In order to verify the encapsulation of calcium phosphate on the emulsion surface, the particle size was monitored using DLS. With each layer deposited on the emulsion surface the various thicknesses of calcium phosphate are shown in FIG. 4. By constantly adding the calcium phosphate, from 0 to 680 mM, the particle size increased from 280 nm to 1400 nm in diameter (FIG. 4(a)). The coating thickness was calculated by subtracting the particle size from the initial size (281 nm) from 0 to 27 mM. The thickness was increased to 38 nm in 27 mM of the added calcium ion.

Figure 5:
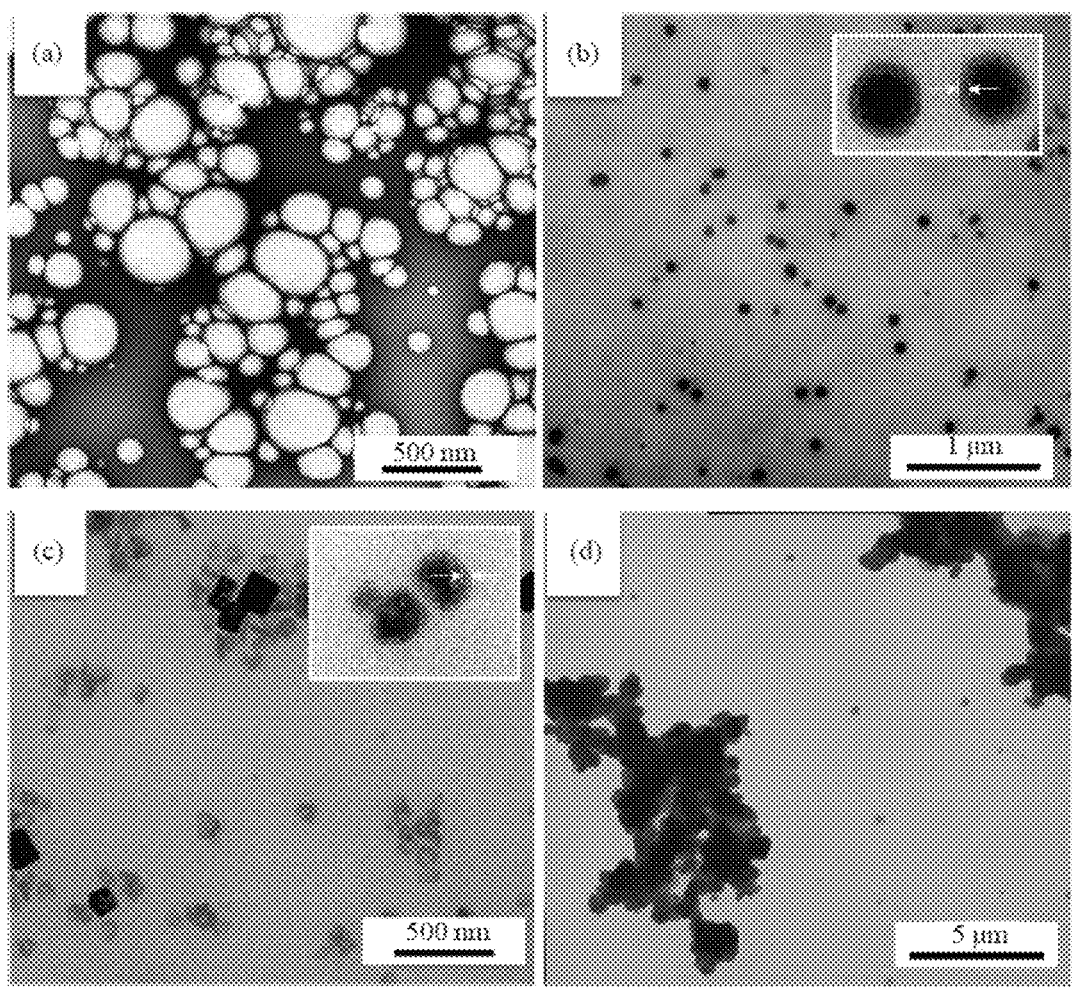
FIG. 5 depicts transmission electron microscope (TEM) photographs of a calcium phosphate (CaP)-coated emulsion according to the present invention.

FIG. 5 shows transmission electron microscopy images of the emulsion and the calcium phosphate (CaP)-coated emulsion. (a). FIG. 5(a) is an image of the negatively stained emulsion before coating. The emulsion size was 227.1 nm (+/−128.7 nm), statistics calculated from 20 particles. FIG. 5(b) shows synthetic red blood cells having an ideal coating thickness (about 10 nm), and is an image of the CaP-coated emulsion with 14 mM of added calcium and phosphate. The particle size was calculated based on 20 particles with an average of 250.4 nm (+/−50.2 nm). The particle has a dark core with a lighter outline, which suggested proper formation of the calcium phosphate shell, with a measured thickness of 11 nm (+/−3 nm). This is similar to the value calculated from DLS. FIG. 5(c) is an image of the particles formed by adding 40 mM of calcium and phosphate solutions, and shows coated synthetic red blood cells and calcium phosphate particles formed of crystal, when calcium phosphate coating (coating thickness: 22 nm) reached limitation. Once the addition exceeded 30 mM, the calcium phosphate crystal was also formed in the system. There were few emulsion particles, coated with CaP, with an average particle size of 320.7 nm (+/−133.6 nm). FIG. 5(d) shows that when the limitation of coating was exceeded, most particles changed to calcium phosphate crystals. The addition of calcium and phosphate was 650 mM, and all of the particles aggregated. The size of aggregations, measured by dynamic light scattering, was about 1300 nm (+/−250 nm).

In the TEM images of FIG. 5, the uncoated emulsion was prepared with a negative stain (FIG. 5(a)), revealing a uniform particle of 227.1 nm (+/−128.7 nm), when coated with CaP (27 mM calcium), the particle grew to 250.4 nm (+/−50.2 nm). The micrographs show a dark core with a light shell, a result of the electrons scattering off axis by elastic nuclear interaction known as Rutherford scattering. Darker regions of the micrograph occur due to increased elastic scattering cause by a fixed mean free path, indicative of a thicker coating or higher atomic number elements. The molecular weight of PFOB ($C_8F_{17}Br$, 498.87 g/mol) is greater than calcium phosphate ($Ca_3(PO_4)_2$, 310.18 g/mol) and brushite ($CaHPO_4 \cdot 2H_2O$, 172.09 g/mol). Therefore, the darker core image (FIG. 5(b)) suggested the presence of PFOB, while the lighter area surrounding the particle was defined as the calcium phosphate shell. When the calcium phosphate thickness was increased in FIG. 5(c) and FIG. 5(d), by adding calcium (220 mM), calcium phosphate crystalline began to form on the emulsion, and at 600 mM, aggregation of the particles became apparent. Greater addition of CaP layers resulted in a greater particle size. This is a result of the aggregation that is likely to occur while the samples dry on the TEM grid.

Figure 9:
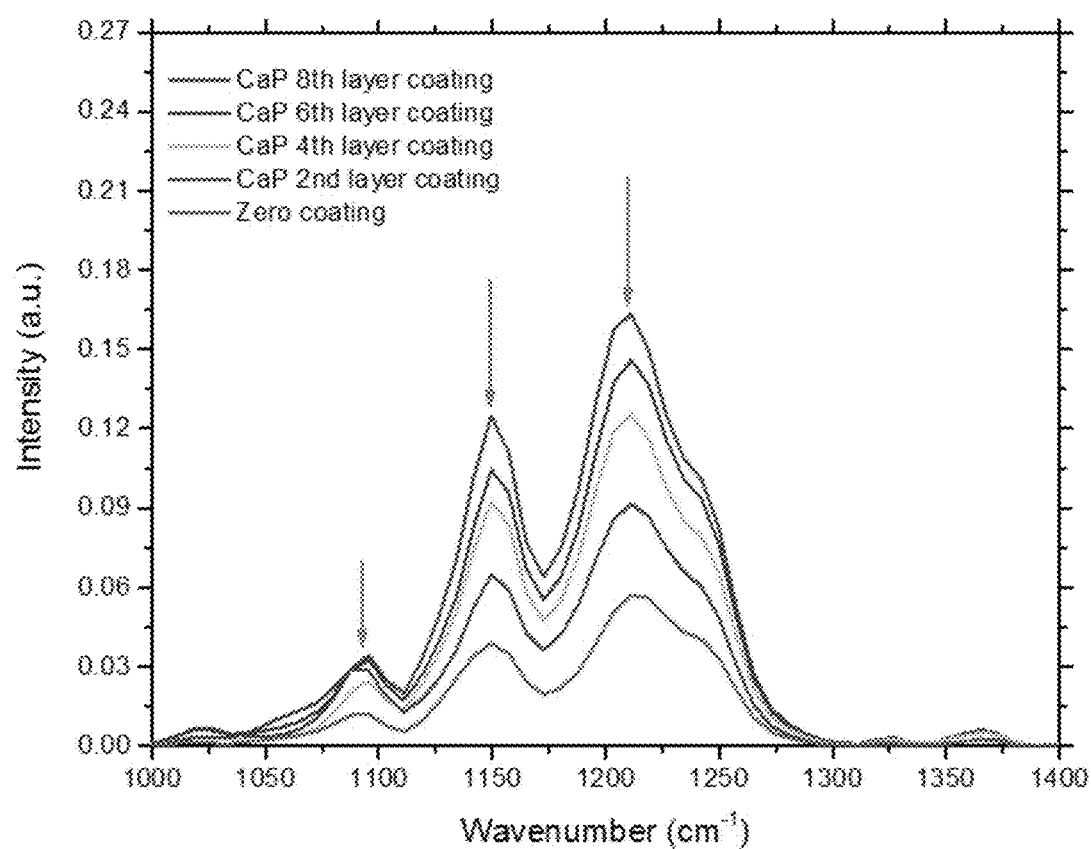
FIG. 9 is a FT-IR graph showing phosphate peaks for the number of calcium phosphate (CaP) coating layers according to the present invention.

As shown in FIG. 9, FT-IR indicated that the intensity of the phosphate peak increased as the number of calcium phosphate coatings increased. The arrow indicates the phosphate peak.

Example 2: Examination of the Rate and Amount of Oxygen Release

Packed red blood cells (RBCs) were hemolyzed with a hypotonic phosphate buffer (5 mM, pH 7.4) to obtain a hemoglobin solution whose concentration was measured by UV-Vis spectroscopy. After determining its raw concentration, the solution was adjusted to 120 µM and pH 7.2. Deoxygenated hemoglobin (Hb) was formed by purging the solution with nitrogen gas until the dissolved oxygen probe was reading zero. In order to measure the rate of oxygen release, Hb and a stopped-flow apparatus (American Instrument Co, Inc, Silver Spring, MY) with a spectrophotometer (Beckman, National Technical Laboratories) were utilized. Four different samples were produced, each with a different number of calcium and phosphate layers. The apparatus was a light-beam path of 4 mm and the slit (0.82 mm). The transmittance of the mixture was recorded using LabView software. By monitoring the change of transmittance at 550 nm, it was shown that Hb was changed to oxygenated hemoglobin ($HbO_2$). The increase of spectra in transmittance at 550 nm was observed over time at 20° C. after rapid mixing of the Hb with the emulsion samples. An average of five successive stopped flow traces were recorded for each sample. The amount of dissolved oxygen was simultaneously determined by the same method as the rate of release. An average of five successive stopped flow traces were recorded for each sample.

Figure 6:
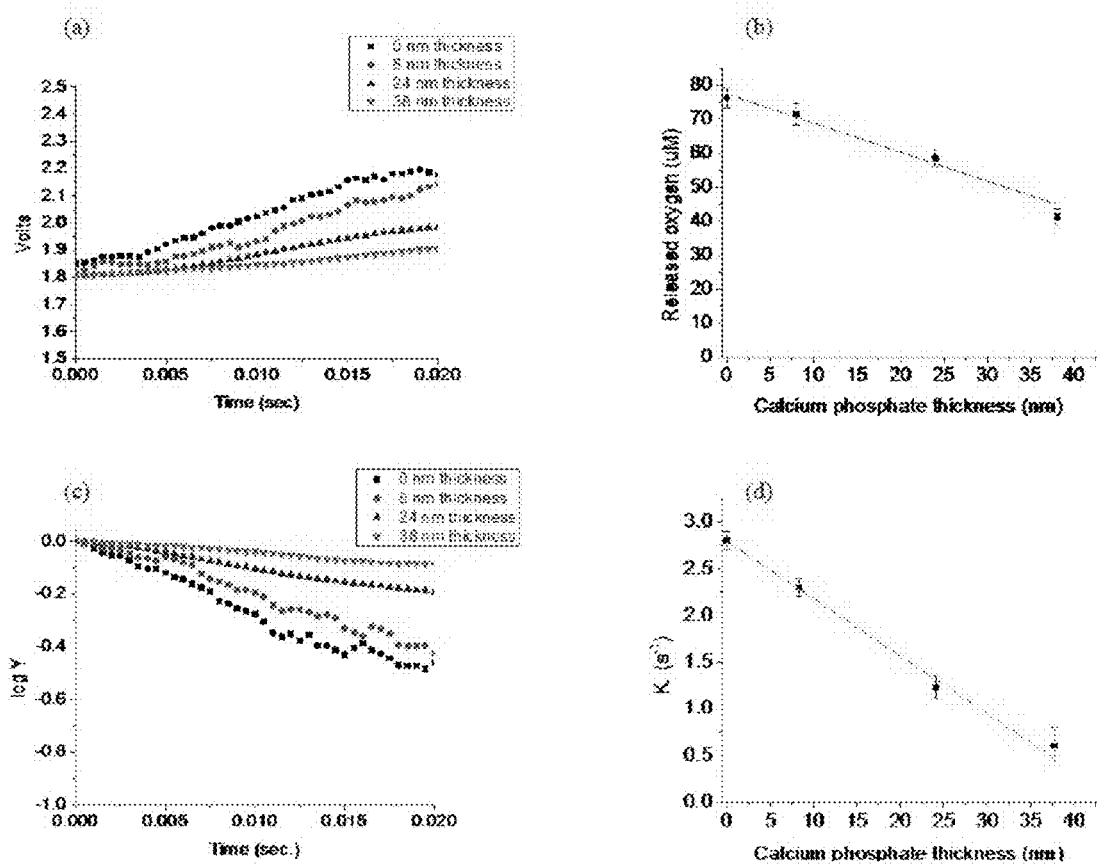
FIG. 6 depicts graphs showing the oxygen capacity and release rate of calcium phosphate (CaP)-coated emulsion particles according to the present invention.

The relationship between the thickness of the coating and amount of oxygen released was studied, and the results showed an increase in coating thickness which caused the amount of oxygen released to drop from 77 µM to 45 µM, and the kinetic constant (k1) decreased from 2.8 $s^{-1}$ to 0.6 $s^{-1}$ (FIG. 6). The mass transport pathway starts with the soy lecithin monolayer, after which the oxygen must travel through the calcium phosphate shell.

The total length of the Soy Lecithin molecule, including head group and tail, is 5.03 nm, and the thickness of the calcium phosphate coating is 8-38 nm. It was expected that the diffusion time for the coated emulsion would be significantly longer than that of the uncoated particle due to the extra barrier.

Even though hemoglobin has four positions to which oxygen can associate itself, this study was only concerned with the kinetics of the first oxygen to bind to the Hb because the other three are non-linearly related to each other with respect to time. Therefore, when a pseudo first-order reaction was assumed, Equation 1 was used to calculate the first order kinetics rate coefficient ($k_{a1}$).

$$\frac{d[HbO_2]}{dt} = -k_a[HbO_2] \quad (1)$$

where [HbO$_2$] is the concentration of the oxygenated Hb, t is the time for the first binding reaction, and Y is the fraction of hemoglobin absorbance at 550 nm.

By plotting the logarithm of Y as a function of time, $k_{a1}$ was obtained from the slope. According to this relation, $k_{a1}$ showed a lower value with a thicker coating, which confirmed the idea that the coating thickness controlled the release oxygen. The amount of oxygen inside the coated particle was less than the uncoated emulsion; hence, the oxygen uptake by Hb was lower than the uncoated emulsion. In order to verify the final oxygen content in the samples the reaction was continuously monitored until the transmittance level plateaued. The thicker calcium phosphate coating resulted in a longer diffusion time of oxygen across the interface.

According to the oxygen dynamics measured by transmittance as shown in FIG. 6, FIG. 6(*a*) shows transmittance as a function of time and coating thickness; FIG. 6(*b*) shows the amount of released oxygen as a function of coating thickness; FIG. 6(*c*) shows the logarithm of the absorbance versus time for the Hb and calcium phosphate-coated emulsion; and FIG. 6(*d*) shows the first order kinetic constant of the oxygen uptake by Hb with the mean and standard deviation taken from five measurements. As the coating thickness increased, the oxygen uptake by Hb was reduced. Namely, as shown in FIG. 6, as the coating thickness of the emulsion increased, the Hb was less saturated with oxygen, and there was a difference in oxygen release ability according to the average particle size. Furthermore, it can be seen that increasing the coating layer thickness slowed and reduced the amount of oxygen absorbed by hemoglobin. Thus, when the thickness of the coating layer is controlled, the synthetic red blood cells of the present invention may have the ability to deliver oxygen to a distant tissue without immediately releasing oxygen.

Example 3: Measurement of Maximum Dosage by Viscosity of Whole Blood

The calcium phosphate-coated nanoemulsion was added to porcine whole blood, and the viscosity of the whole blood was measured. The results of the measurement are shown in FIG. 7. From the measured viscosity of the whole blood, the maximum dosage was determined to be 33 mg/mL. At a dosage of 35 mg/mL, it appears that the nanoemulsion particles destroy blood systems such as red blood cells, and thus the viscosity of the whole blood is reduced. Therefore, when the dosage was greater than 35 mg/mL, the protein in the blood interacted with the calcium from the nanoparticle coating, resulting in an increase in the viscosity.

Example 4: Hematocrit

Figure 8:
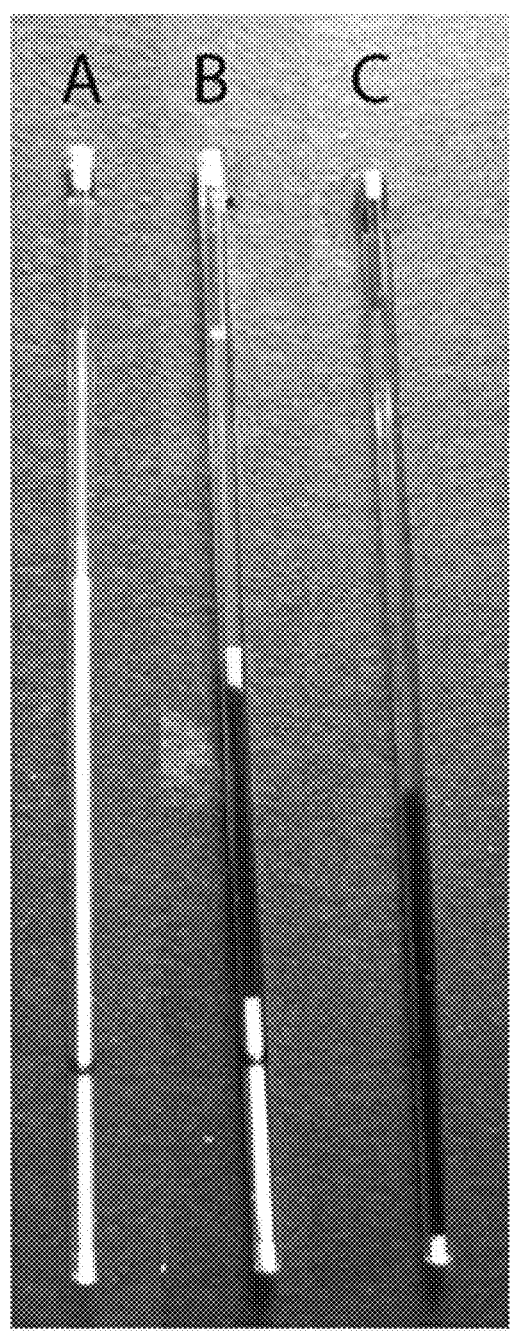
FIG. 8 depicts photographs showing the results of centrifuging a calcium phosphate (CaP)-coated emulsion of the present invention by a hematocrit centrifuge.

Hematocrit is a result obtained by centrifugation. FIG. 8(A) shows separation of coated artificial blood cells from whole blood by centrifugation; FIG. 8(B) shows coated cells separated from whole blood; and FIG. 8(C) shows that red blood cells (red) and serum (transparent) are present in centrifuged whole blood.

FIG. 8(A) shows the calcium phosphate-coated nanoemulsion, and the white region in the FIG. 8(A) indicates the nanoemulsion. In the semi-transparent region in the upper end, there are little or no lightweight nanoemulsion particles, because the inside of the particles is filled with water. FIG. 8(B) shows the results obtained by mixing whole blood with the nanoemulsion at a volume ratio of 1:1 and centrifuging the sample by a hematocrit centrifuge. The white region in FIG. 8(B) indicates the nanoemulsion, and the red color indicates red blood cells. The upper red semi-transparent region indicates plasma, and the dosage of the nanoemulsion was 33 mg/mL. FIG. 8(C) shows whole blood used in an example of the present invention. The blood contains 50 vol % of red blood cells and 50 vol % of plasma.

INDUSTRIAL APPLICABILITY

Homogeneous nanoemulsion having a thickness-controllable coating composed of $Ca^{2+}$ and $PO_4^{2-}$ according to the present invention can be obtained in high yield by uniformly coating $Ca^{2+}$ ions on a perfluorooctyl bromide-containing lecithin emulsion and coating $PO_4^{2-}$ ions thereon.

Furthermore, the oxygen release rate of the nanoemulsion can be controlled by changing the coating thickness. The distance by which oxygen is transported in the human body varies. For this reason, when the rate of oxygen release from the nanoemulsion is made slower, the nanoemulsion can transport a sufficient amount of oxygen from the first place, into which the nanoemulsion was introduced, to a distant place. In addition, the coating has the effect of protecting the nanoemulsion from the protein in blood.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. Synthetic red blood cells, comprising:
   (A) a lecithin emulsion comprising a perfluorinated compound; and
   (B) a calcium phosphate (CaP) coating layer consists of a $Ca^{2+}$ coating layer formed on a surface of the lecithin emulsion and a $PO_4^{2-}$ coating layer formed on the $Ca^{2+}$ coating layer,
   wherein the CaP coating layer consists of 1 to 10 layers.

2. The synthetic red blood cells of claim 1, wherein a particle size of the synthetic red blood cells is 90-1600 nm.

3. The synthetic red blood cells of claim 1, wherein a thickness of the CaP coating layer is 5-150 nm.

4. The synthetic red blood cells of claim 1, wherein the perfluorinated compound is selected from the group consisting of perfluorooctyl bromide (PFOB), perfluorodecyl bromide (PFDB), perfluorodichlorooctane (PFDCO), perfluorohexane (PFH) and perfluorooctane (PFO).

5. The synthetic red blood cells of claim 1, wherein lecithin is L-α-phosphatidylcholine extracted from soybean, sunflower or egg yolk.

6. A method of preparing synthetic red blood cells by a layer-by-layer coating method, the method comprising:
   (a) forming a $Ca^{2+}$ coating layer on a surface of an emulsion having a predetermined pore size by adding a solution of a $Ca^{2+}$ ion-containing compound to the emulsion, and then forming a $PO_4^{2-}$ coating layer on the $Ca^{2+}$ coating layer by adding a solution of a $PO_4^{2-}$ ion-containing compound; and
   (b) removing residual ions which are not absorbed into the emulsion by dialysis,
   wherein the step (b) is performed 1-10 times.

7. The method of claim 6, wherein the emulsion in the step (a) is prepared by a method comprising:
   (a-1) forming an emulsion by adding and stirring lecithin, a perfluorinated compound and water; and (a-2) extruding the emulsion to a membrane having a pore size of 200-300 nm.

8. The method of claim 6, which the perfluorinated compound is selected from the group consisting of perfluorooctyl bromide (PFOB), perfluorodecyl bromide (PFDB), perfluorodichlorooctane (PFDCO), perfluorohexane (PFH) and perfluorooctane (PFO).

9. The method of claim 6, wherein the step (a) is performed at room temperature.

10. The method of claim 6, wherein the step (b) is performed 7 to 10 times so that an emulsion having a particle size of 280 nm or less is uniformly dispersed.

11. The method of claim 6, wherein the $Ca^{2+}$ ion-containing compound is one or more selected from the group consisting of calcium chloride, calcium hydroxide, calcium nitride, calcium carbonate and calcium acetate, a concentration thereof is 5-30 mM, and pH thereof is 7.5-12.

12. The method of claim 6, wherein the $PO_4^{2-}$ ion-containing compound is one or more selected from the group consisting of phosphoric acid, potassium phosphate, sodium hydrogen phosphate and ammonium phosphate, a concentration thereof is 5-30 mM, and pH thereof is 7.2-12.6.

* * * * *